(12) United States Patent
Pfeifer et al.

(10) Patent No.: US 6,493,085 B1
(45) Date of Patent: Dec. 10, 2002

(54) LIGHT ANALYZER APPARATUS

(75) Inventors: John Edward Pfeifer, Redding; William Frederick, Bridgeport; Alvaro Dedios, Norwalk; Stephen C. Fog, New Canaan, all of CT (US)

(73) Assignee: Microcensus, LLC, Bethel, CT (US)

( * ) Notice: Subject to any disclaimer, the term of this patent is extended or adjusted under 35 U.S.C. 154(b) by 0 days.

(21) Appl. No.: 09/578,323

(22) Filed: May 24, 2000

(51) Int. Cl.[7] .................. G01N 21/01; G01N 21/59
(52) U.S. Cl. ............................. 356/436; 356/440
(58) Field of Search ..................... 356/432, 433, 356/434, 435, 436, 440, 441, 442; 422/82.09

(56) References Cited

U.S. PATENT DOCUMENTS

| | | | |
|---|---|---|---|
| 3,877,817 A | 4/1975 | Ralston | 356/180 |
| 3,939,687 A | 2/1976 | Waldron | 73/1 |
| 3,994,590 A | 11/1976 | Di Martini | 356/178 |
| 4,027,979 A | 6/1977 | Komarniski | 356/180 |
| 4,066,362 A * | 1/1978 | Carter | 356/440 |
| 4,392,746 A | 7/1983 | Rook et al. | 356/409 |
| 4,475,823 A | 10/1984 | Stone | 374/1 |
| 5,013,155 A | 5/1991 | Rybak | 356/408 |
| 5,092,677 A * | 3/1992 | Curtis | 356/435 |
| 5,115,860 A * | 5/1992 | Hayashi | 356/341 |
| 5,144,814 A | 9/1992 | Gaudette | 62/225 |
| 5,307,144 A | 4/1994 | Hiroshi et al. | 356/244 |
| 5,345,064 A | 9/1994 | Hesse | 219/505 |
| 5,677,134 A | 10/1997 | Hayashi et al. | 435/7.4 |
| 5,703,342 A | 12/1997 | Hoffmann et al. | 219/497 |
| 5,770,389 A | 6/1998 | Ching et al. | 435/7.92 |
| 5,903,346 A | 5/1999 | Rinke et al. | 356/320 |
| 5,959,738 A | 9/1999 | Hafeman et al. | 356/440 |
| 5,985,653 A | 11/1999 | Armstrong | 435/303.1 |
| 6,004,029 A | 12/1999 | Moslehi et al. | 374/1 |
| 6,010,243 A | 1/2000 | Hessler et al. | 374/1 |

* cited by examiner

*Primary Examiner*—Richard A. Rosenberger
(74) *Attorney, Agent, or Firm*—David P. Gordon; David S. Jacobson; Thomas A. Gallagher

(57) ABSTRACT

A light analysis system for analyzing light transmitted through an ampoule includes a housing having at least one receptacle for the ampoule, a cover for substantially preventing ambient light from affecting the receptacle and having an interior reflective surface, and a master control system. Each receptacle includes at least one light source and a photodetector positioned such that the light from the light source passes through the receptacle (and thereby the ampoule and its contents) prior to entering the photodetector. According to one preferred aspect of the invention, the receptacles are provided preferably at a 30° to 45° angle relative to vertical. According to another preferred aspect of the invention, the light source is at least one LED which is directed to transmit light upward into the reflective surface of the cover such that the light is reflected by the cover downward into the receptacle toward the photodetector. The master control system permits user input, operates the light analysis system, and provides a user-readable display for the output of the results of the light analysis of the contents of the ampoule in the receptacle. The apparatus may include a large number of receptacles suitable for laboratory use or may include fewer or one receptacle suitable for home or portable use. Power supply circuitry is provided facilitating the use of the apparatus in a variety of environments.

19 Claims, 3 Drawing Sheets

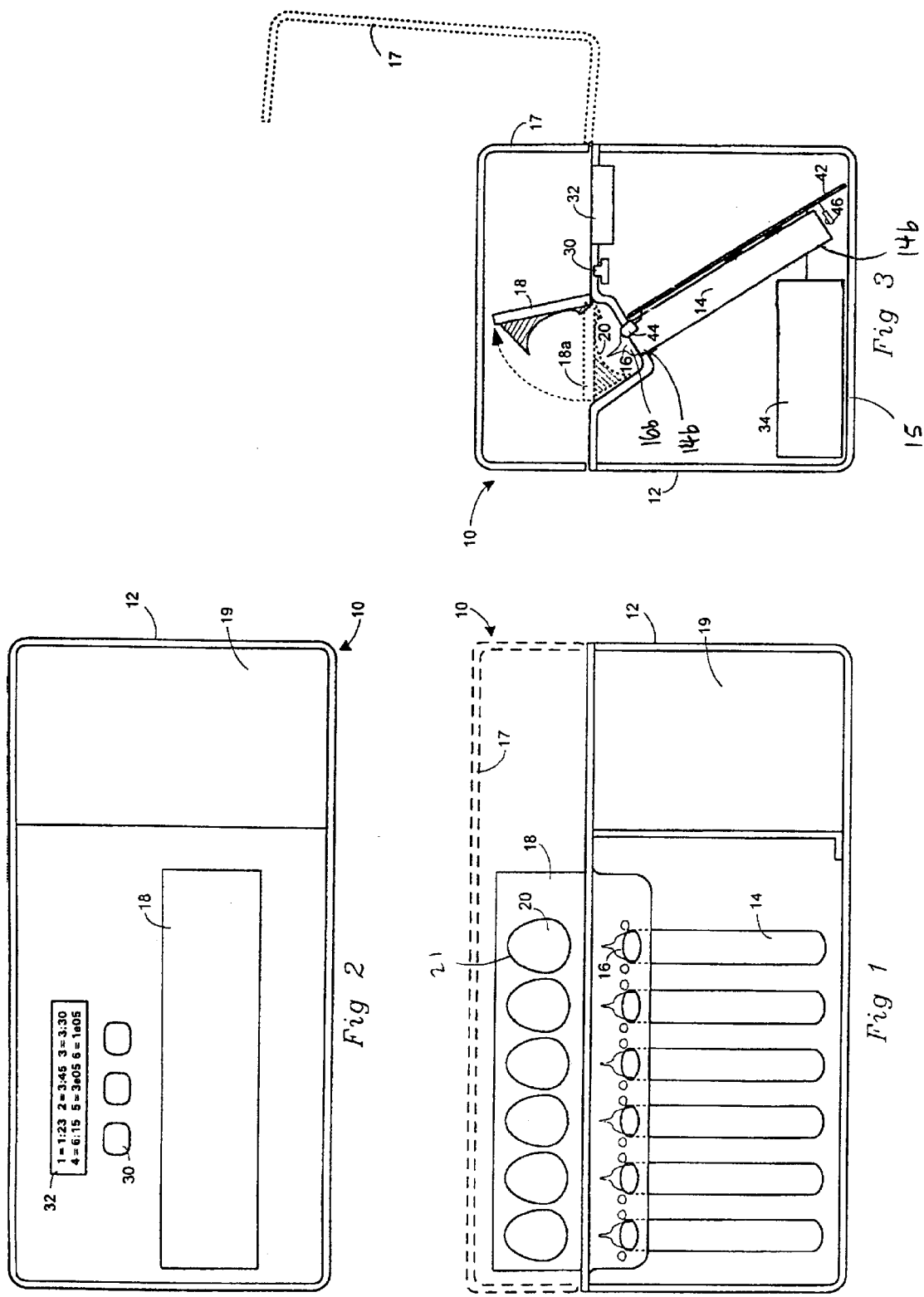

LIGHT ANALYZER APPARATUS

This application is related to co-pending application Ser. No. 09/557,653 entitled "Incubation System for a Light Analyzer Apparatus", filed Apr. 25, 2000, which is hereby incorporated by reference herein in its entirety.

BACKGROUND OF THE INVENTION

1. Field of the Invention

This invention relates broadly to analytical instruments. More particularly, this invention relates to light analysis and power systems for an analyzer apparatus.

2. State of the Art

Analysis systems require that a test sample be subject to light analysis to determine the contents or a change in contents of the sample. For example, water test kits are used to determine the bacteriological activity within water. In some water test kits, a water sample is taken in an ampoule containing an enzyme or reagent, thereby causing a colorimetric change to the water. The light transmitted through the water sample is then measured to determine the contents of the ampoule.

While the prior art does include a number of analysis systems, such existing systems have a number of serious drawbacks. First, many analyzers are often bulky. The bulk reduces the portability of the device and inhibits the use of such a device in the field. In fact, most analyzers are not intended to be portable and therefore generally have limitations on the type of power input which can be used to power the system.

Second, where light is axially transmitted through an ampoule containing a sample, a large number of components are often required at both ends of the ampoule for light emission and light detection. However, this configuration requires a relatively larger apparatus and also requires that the circuitry be spread out throughout the apparatus.

SUMMARY OF THE INVENTION

It is therefore an object of the invention to provide an apparatus which centralizes all componentry of the light emission and detection system.

It is another object of the invention to provide a light analysis apparatus which is substantially free from error due to ambient light.

It is also an object of the invention to provide a light analysis apparatus which is capable of operating with a variety of power sources.

It is a further object of the invention to provide a portable and relatively low cost light analysis apparatus.

In accord with these objects, which will be discussed in detail below, a light analysis system for analyzing light transmitted through an ampoule is provided. The light analysis system includes a housing having at least one receptacle (or nest) for an ampoule, a cover for substantially preventing ambient light from affecting each receptacle and having an interior reflective surface, and a master control system. Each receptacle includes at least one light source and a photodetector positioned such that the light from the light source passes through the receptacle (and thereby the ampoule and its contents) prior to entering the photodetector. According to one preferred aspect of the invention, the receptacles are provided preferably at a 30° to 45° angle relative to vertical. According to another preferred aspect of the invention, the light source is at least one LED which is directed to transmit light upward into the reflective surface of the cover such that the light is reflected by the cover downward into the receptacle toward the photodetector.

The master control system permits user input, operates the light analysis system, and provides a user-readable output which displays the results of the analysis of the contents of the ampoule in the receptacle.

The apparatus may include a large number of receptacles suitable for laboratory use or may include fewer or even a single receptacle suitable for home or portable use. Power supply circuitry is provided facilitating the use of the apparatus in a variety of environments, e.g., in the field, in a laboratory, or in a vehicle.

Additional objects and advantages of the invention will become apparent to those skilled in the art upon reference to the detailed description taken in conjunction with the provided figures.

BRIEF DESCRIPTION OF THE DRAWINGS

FIG. 1 is a partial front view of the light analysis apparatus of the invention;

FIG. 2 is a top view of the apparatus of the invention without the case lid;

FIG. 3 is a partial side view of the apparatus of the invention showing the case lid in open and closed positions;

DETAILED DESCRIPTION OF THE PREFERRED EMBODIMENTS

Figure 4:
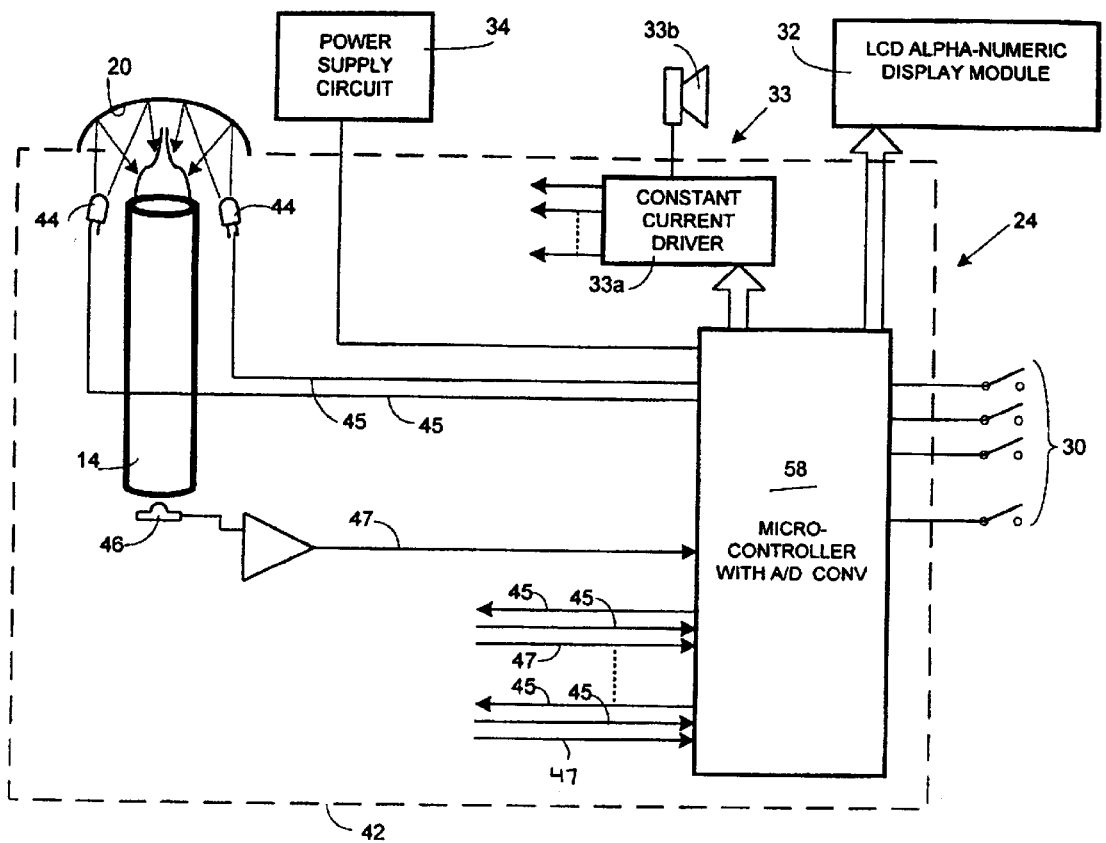
FIG. 4 is a partial schematic circuit diagram of a master control system of the apparatus of the invention.

Turning now to FIGS. 1 through 3, an ampoule incubator and analyzer 10 according to the invention includes a housing 12 having preferably six receptacles (nests) 14, each for receiving an ampoule 16, and preferably a housing lid 17 movable between closed and open (broken lines) positions. The housing 12 preferably also includes a preferably planar lower surface 15 which is adapted to seat the housing on a planar surface, and a storage area 19 for storing ampoules or other items. A receptacle cover 18 in an open position provides access to the receptacles and in a closed position 18a substantially individually seals each receptacle to prevent ambient light from affecting the receptacle. The receptacle cover 18 preferably includes a plurality of concave portions 21 each having a diffuse reflective interior surface 20 which reflects and distributes light from a light source, discussed below, through the receptacles.

Figure 7:
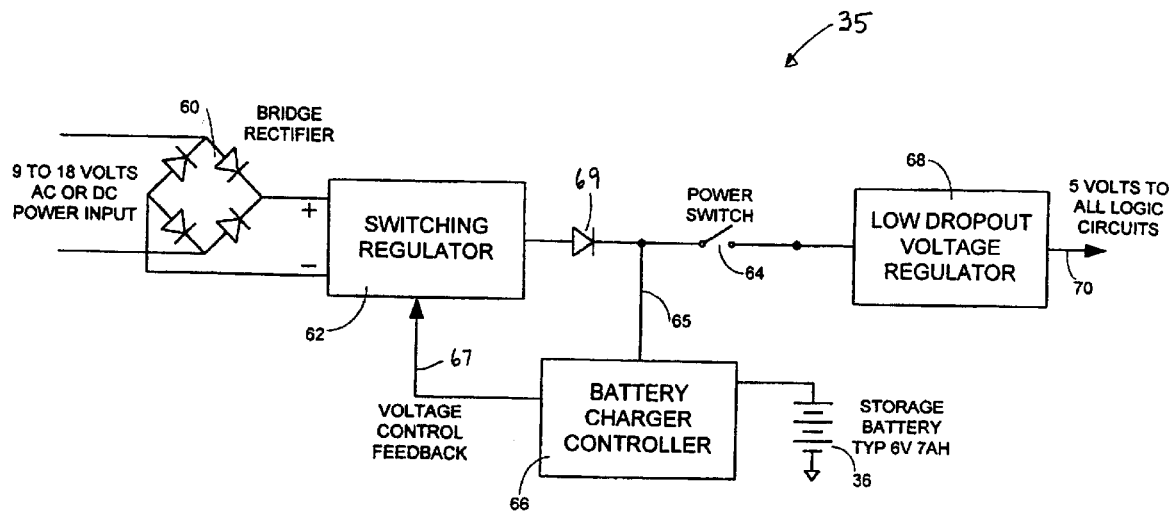
FIG. 7 is a schematic of a power source for the light analysis system of the invention.

Referring to FIG. 4, the analyzer 10 also includes a master control system 24. The master control system 24, which includes a microcontroller 58, generally permits user input through control buttons 30 and provides information to a user-readable display 32 and a signal to an audio output 33 comprised of a driver chip 33a and a sound transducer 33b for the output of the results of testing with the analyzer. The master control system 24 also operates, for each receptacle, the associated light source and an optical detector, discussed in detail below. A power supply 34 including a battery 35 and appropriate circuitry 36 to power the various systems is also provided (FIG. 7).

Figure 5:
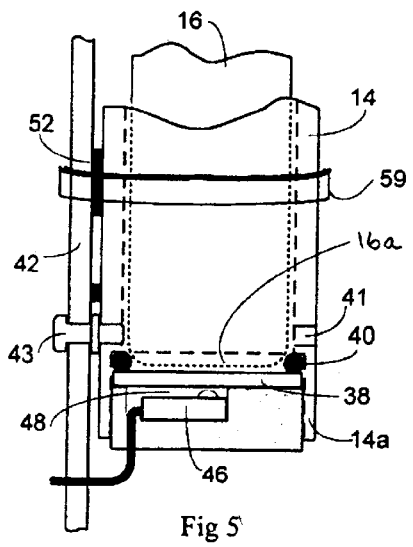
FIG. 5 is a partial side view of an ampoule receptacle according to the invention.
Figure 6:
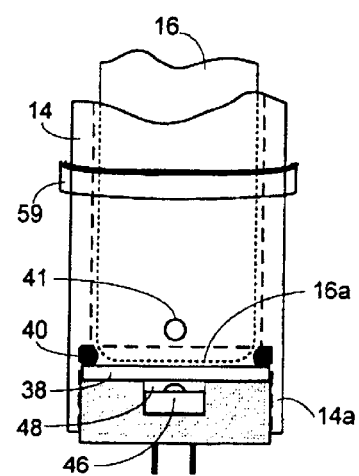
FIG. 6 is a partial front view of an ampoule receptacle according-to the invention.

Referring to FIG. 3, more particularly, each receptacle is an opaque tube; e.g., metal or plastic, approximately 0.5–0.625 inch in diameter, and preferably approximately four inches in length. Turning to FIGS. 5 and 6, a transparent preferably cleanable disk 38, preferably glass or polycarbonate, is provided near a lower end 14a of the receptacle. The closed end 16a of the ampoule 16 is provided near the disk 38 (FIGS. 5 and 6), with the open end 16b of the ampoule at the upper end 14b of the receptacle (FIG. 3). An O-ring 40 provides a watertight seal between the disk 38 and the interior surface of the receptacle 14. A weep hole 41 is provided in the receptacle adjacent but above the location of the disk 38 to permit any water, test solution, or cleaning/sterilization solution which may drip into the receptacle 14 to drain therefrom.

Referring to FIGS. 3 through 6, the receptacles 14 are attached to a printed circuit board (PCB) 42, e.g., by screws 43, preferably such that a longitudinal axis of each receptacle runs parallel to the plane of the PCB. Each receptacle 14 is provided with a light source 44 and an optical detector 46, each coupled to the master controller 24. Both the light source 44 and optical detector 46 are also preferably physically coupled to the PCB 42. The light source 44, preferably including one or more LEDs, is adapted to emit light into the receptacle 14 when receiving a signal 45 from the master controller 24. In accord with a preferred aspect of the invention, the light source is a plurality of LEDs 44 coupled to the PCB 42 in an orientation such that they direct light into the reflective interior surface 20 of the associated portion 21 of the cover 18 of housing 12. The reflective surface 20 scatters the light of the LEDs 44 through the ampoule 16 in the receptacle 14 and toward the detector 46 located at the lower end 14a of the receptacle (FIG. 3). A preferably hemispherical lens 48 is preferably provided to gather the scattered light and channel the light transmitted through the ampoule 16 toward the detector 46 (FIGS. 5 and 6). The optical detector 46 provides a signal 47 to the microcontroller 58 which analyzes the signal.

Referring to FIG. 3, the receptacles are preferably provided at an oblique, non-perpendicular angle relative to both the vertical and the horizontal, e.g., 30° to 45° off vertical, by angling the receptacles relative to the lower surface 15 of the housing 12. The angle of the receptacles facilitates light transmission through the ampoules by preventing sediment from accumulating on the entire bottom of the ampoule and thereby blocking all light paths between the reflective surface 20 and the optical detector 46. Moreover, an ampoules often includes a stirring rod which will settle outside a direct axial light path when the receptacles are angled. As the receptacles are preferably coupled to the PCB 42, one preferred manner of providing the angle is to orient the entire PCB at the desired angle relative to vertical within the housing 12. The above described configuration of the light source 44, optical detector 46, and orientation of the receptacles 14 provides a system in which all componentry is preferably provided at or below the level of the top of the ampoule 16. This configuration facilitates sealing the receptacles from ambient light, with the reflective surface 20 of the cover providing the redirection of the light into the required path through the receptacle and ampoule. In addition, as the cover is capable of reflecting the light, the need for separate reflectors is obviated and a system with fewer components, and therefore lower cost, is provided.

The light source may be adapted to emit light at one or more wavelengths according to any known analysis system in the art. For example, all LEDs in the light source may emit the same wavelength, or the light source may include LEDs which emit light at different wavelengths. The master control system may be operated to cause all the LEDs to emit light constantly, alternatingly, or to be pulsed. The master control system may be programmed to operate the light system for photometric or colorimetric analysis, which are described in various forms and in detail in U.S. Pat. No. 5,959,738 to Hafeman et al., U.S. Pat. No. 5,903,346 to Rinke et al., U.S. Pat. No. 5,770,389 to Ching et al., U.S. Pat. No. 5,307,144 to Hiroshi et al., U.S. Pat. No. 5,013,155 to Rybak, U.S. Pat. No. 4,392,746 to Rook et al., U.S. Pat. No. 4,027,979 to Komarniski, U.S. Pat. No. 3,994,590 to Di Martini et al., U.S. Pat. No. 3,877,817 to Ralston, which are hereby incorporated by reference herein in their entireties.

According to another preferred aspect of the invention, the analyzer 10 may be provided with circuitry to permit the use-of a wide variety of power sources, e.g., AC current, car batteries, standard outlets, to facilitate use wherever required. Referring to FIG. 7, the power supply 34 includes a circuit 35 including a bridge rectifier 60 which receives AC or DC power. The AC power can be from 9V to 18V with a plug transformer, and the DC power can be a battery having ±9V to ±16V. The bridge rectifier 60 functions as a polarity guard and rectifies all the voltage to a positive value. The power is sent from the bridge rectifier 60 to a switching regulator 62. The switching regulator 62 is a DC to DC converter which handles the required range of possible input voltages and provides a substantially constant output of approximately 7 volts. After the switching regulator 62, a solid state power switch 64, e.g., an FET, is provided for operating the analyzer. In addition, a path 65 from a battery charger controller 66 to the power switch 64 is also provided. When the power switch 64 is in a closed position, the 7V from the switching regulator passes through the switch 64 and to a low dropout voltage regulator 68 which consistently produces 5V which is sent to all circuits in the apparatus. When the power switch 64 is in an open position, the battery charger controller 66 receives the 7V from the switching regulator 62 and operates to charge the battery 36. This is facilitated through a voltage control feedback 67 which charges the battery to a maximum charge without overcharging to thereby enhance the performance and life of the battery. The battery 36 is preferably a 6V, 7 amp/hour storage battery. A diode 69 is provided between the battery charger controller 66 and the switching regulator 62 to prevent discharge of the battery 36 when the power switch 64 is open and no power input is across the regulator 62. When the power switch 64 is in a closed position and the apparatus is disconnected from an AC or external DC power source, the battery 36 provides 6V to the voltage regulator 68, which is then converted to transistor logic, e.g., 5V, to power the circuits. As the voltage regulator 68 is a low dropout regulator, it consistently produces 5V at 70 and does not require substantial headroom to regulate down. Therefore, even as the charge on the battery is decreased through usage, e.g., to 5.25V, the regulator still operates to produce a constant transistor logic. According to the invention, a 6V, 7 amp/hour storage battery conditioned by the battery charger controller 66 can continuously operate the master control system 24 and the light analysis systems and all other circuitry for six receptacles for at least seventeen hours.

Figure 8:
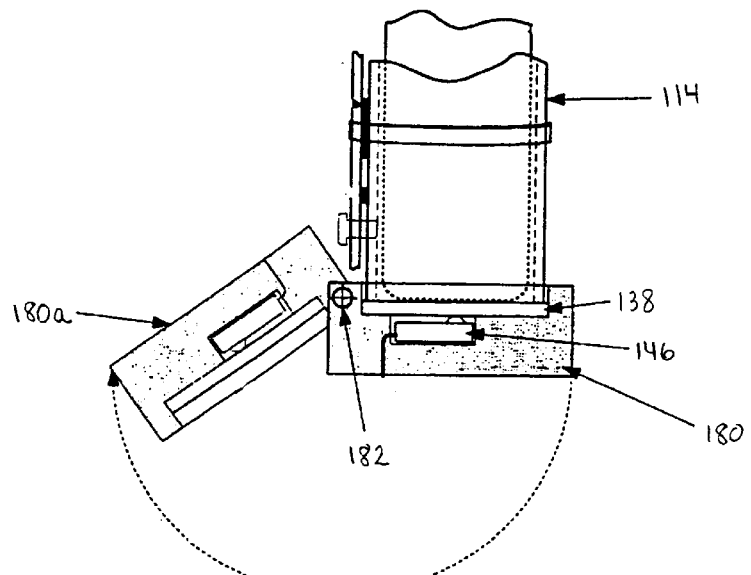
FIG. 8 is a partial side view of a second embodiment of an ampoule receptacle according to the invention.

Turning now to FIG. 8, according to another embodiment of the invention, substantially similar to the first (with like parts having numbers incremented by 100), the receptacle 114 is a tubular member having a closed end 114a defined by a hinged end cap 180. The hinged end cap 180 is rotatable about a hinge 182 between closed 180 and open 180a positions. The photoreceptor 146 and disk 138 are provided in the end cap 180. The receptacle 114 is preferably oriented within the housing such that the end cap 180 is provided adjacent a side of the housing (i.e., preferably not located on the bottom of the housing) such that the end cap does not interfere with stable seating of the light analysis system. When the end cap is in the open position, access into the interior of the receptacle is provided. As such, the receptacle is adapted to be cleaned without the use of a weep hole, as required in the first embodiment, and the potential problem of what to do with fluid draining from a weep hole.

There have been described and illustrated herein an embodiment of a light analysis system. While a particular embodiment of the invention has been described, it is not intended that the invention be limited thereto, as it is intended that the invention be as broad in scope as the art will allow and that the specification be read likewise. Thus, while LEDs have been disclosed for the light source, it will be appreciated that other light sources may be used as well. In addition, while the apparatus has been described with six independently operable receptacles, the apparatus may include a larger number (e.g., 24 to 36) of receptacles such that it is suitable for laboratory use or may include fewer or even a single receptacle suitable for home or portable use. It will therefore be appreciated by those skilled in the art that yet other modifications could be made to the provided invention without deviating from its spirit and scope as claimed.

What is claimed is:

1. A light analysis system, comprising:
   a) a housing having-a lower surface and-a cover having an interior reflective surface and movable between open and closed positions;
   b) at least one receptacle in said housing having first and second ends and defining a longitudinal axis;
   c) for each said receptacle, a light source which emits light; and
   d) for each said receptacle, a light detector which detects said light emitted by said light source,
   wherein when said cover is in said open position access is provided to said at least one receptacle, and when said cover is in said closed position, said cover substantially prevents ambient light from entering said at least one receptacle and said reflective surface reflects said light toward said light detector.

2. A light analysis system according to claim 1, wherein: said longitudinal axis of each said receptacle is oriented at an oblique, non-perpendicular angle relative to said lower surface.

3. A light analysis system according to claim 2, wherein: said angle is between 30° and 45° relative to a perpendicular to said lower surface.

4. A light analysis system according to claim 2, wherein: said angle is between 30° and 45° relative to vertical.

5. A light analysis system according to claim 1, further comprising:
   e) a printed circuit board to which said at least one receptacle and its associated light source and light detector are coupled.

6. A light analysis system according to claim 1, wherein: for each said receptacle, said light source is oriented to emit said light in a direction which is non-axial with said longitudinal axis.

7. A light analysis system according to claim 1, wherein: for each said receptacle, said second end includes said light detector and a seat on which an ampoule can be seated.

8. A light analysis system according to claim 1, wherein: for each said receptacle, said second end includes a light gathering lens and said light detector.

9. A light analysis system according to claim 1, wherein: said light source comprises at least one LED.

10. A light analysis system according to claim 1, further comprising:
    e) a control system which permits user operation of said light analysis system.

11. A light analysis system according to claim 1, further comprising:
    e) circuitry adapted to regulate and convert an AC or DC voltage source to a consistent DC voltage, said consistent DC voltage powering said light source and said light detector.

12. A light analysis system according to claim 1, wherein: said interior reflective surface includes a concave reflective portion for each of said at least one receptacle.

13. A light analysis system according to claim 1, wherein: each said receptacle comprises a tubular portion and an end cap, said end cap being rotatable relative to said tubular portion such that when rotated into an open position access into said tubular portion is provided.

14. A light analysis system according to claim 13, wherein: each said end cap includes a respective said light detector.

15. A light analysis system restable on a surface, comprising:
    a) a housing a cover having an interior reflective surface and movable between open and closed positions;
    b) at least one receptacle in said housing having first and second ends and defining a longitudinal axis, said longitudinal axis being at an angle relative to vertical when said system is resting on the surface;
    c) for each said receptacle, a light source which emits light; and
    d) for each said receptacle, a light detector which detects said light emitted by said light source,
    wherein when said cover is in said open position access is provided to said at least one receptacle, and when said cover is in said closed position, said cover substantially prevents ambient light from entering said at least one receptacle and said reflective surface reflects said light toward said light detector.

16. A light analysis system according to claim 15, wherein: said angle is 30°–45° relative to vertical.

17. A light analysis system according to claim 15, further comprising:
    e) a printed circuit board, said at least one receptacle being attached to said printed circuit board.

18. A light analysis system according to claim 15, wherein: each said receptacle comprises a tubular portion and an end cap, said end cap being rotatable relative to said tubular portion such that when rotated into an open position access into said tubular portion is provided.

19. A light analysis system according to claim 18, wherein: each said end cap includes a respective said light detector.

* * * * *